(12) United States Patent
Yoo et al.

(10) Patent No.: US 8,199,321 B2
(45) Date of Patent: Jun. 12, 2012

(54) LASER ABLATION APPARATUS AND METHOD

(75) Inventors: Jong Hyun Yoo, Milpitas, CA (US); Randolph S. Tribe, San Jose, CA (US); Chunyi Liu, Union City, CA (US)

(73) Assignee: Applied Spectra, Inc., Fremont, CA (US)

( * ) Notice: Subject to any disclaimer, the term of this patent is extended or adjusted under 35 U.S.C. 154(b) by 373 days.

(21) Appl. No.: 12/435,970

(22) Filed: May 5, 2009

(65) Prior Publication Data

US 2009/0273782 A1 Nov. 5, 2009

Related U.S. Application Data

(60) Provisional application No. 61/126,633, filed on May 5, 2008.

(51) Int. Cl.
*G01J 3/443* (2006.01)
*G01N 21/63* (2006.01)

(52) U.S. Cl. ............................ 356/318; 356/326; 356/72

(58) Field of Classification Search .................. 356/326, 356/72, 318
See application file for complete search history.

(56) References Cited

U.S. PATENT DOCUMENTS

| | | | |
|---|---|---|---|
| 5,656,186 A | 8/1997 | Mourou et al. | |
| 6,587,600 B1 * | 7/2003 | Shipley | 382/284 |
| 7,106,439 B2 * | 9/2006 | Lacour et al. | 356/318 |
| 7,151,609 B2 | 12/2006 | Chalmers et al. | |
| 7,240,839 B2 | 7/2007 | Jung et al. | |
| 7,363,180 B2 | 4/2008 | Swaringen et al. | |
| 7,599,048 B2 * | 10/2009 | Yoo et al. | 356/72 |
| 7,663,749 B2 * | 2/2010 | Levesque et al. | 356/318 |
| 2007/0046934 A1 | 3/2007 | Roy | |
| 2007/0296966 A1 | 12/2007 | Benicewicz et al. | |
| 2008/0037005 A1 | 2/2008 | Bareket et al. | |
| 2008/0070327 A1 | 3/2008 | Ogasawara et al. | |

OTHER PUBLICATIONS

International Search Report and Written Opinion of the International Searching Authority, mailed Dec. 30, 2010, for Application No. PCT/US2010/055327, 9 pages.
International Search Rport dated Jul. 6, 2009, PCT Application No. PCT/US09/42862, Filed May 5, 2009, Applied Spectra, Inc.

* cited by examiner

*Primary Examiner* — Layla Lauchman
(74) *Attorney, Agent, or Firm* — Microtechnology Law & Analysis; Daniel L. Flamm (57) ABSTRACT

Provided is a laser ablation spectroscopy apparatus and method. A pulse laser is focused on the sample site to generate a plasma plume during a laser ablation process. The plasma plume is detected with a spectrometer and an intensified charge coupled device. A sample of material is coupled to a stage movable in the x, y and z directions using an array of x-y-z motors. A change in the height of the sample is detected using a triangulation sensor. The apparatus includes a system computer for synchronizing the movement of the stage in the x, y and z direction during the laser ablation process. The method includes a protocol of generating one or more laser ablations per sample site. The spectral data of the total number of laser ablations for each sample site are averaged together. The protocol includes laser ablating additional sample sites and averaging the spectral data of the total number of sample sites.

48 Claims, 6 Drawing Sheets

LASER ABLATION APPARATUS AND METHOD

This patent application claims priority under 35 U.S.C. 119(e) of the U.S. Provisional Patent Application Ser. No. 61/126,633, filed May 5, 2008, and entitled "LASER ABLATION APPARATUS AND METHOD". The Provisional Patent Application Ser. No. 61/126,633 filed May 5, 2008, and entitled "LASER ABLATION APPARATUS AND METHOD" is also hereby incorporated by reference.

BACKGROUND

Field of the Invention

Restriction of hazardous substances by statutes such as the Directive on the Restriction of the Use of Certain Hazardous Substances in Electrical and Electronic Equipment 2002/95/EC (commonly referred to as the Restriction of Hazardous Substances Directive or RoHS) was adopted in February 2003 by the European Union. The state of California has passed a similar law. The directive restricts the use of six hazardous materials in the manufacture of various types of electronic and electrical equipment. The six hazardous materials include Lead, Mercury, Cadmium, Hexavalent chromium (chromium xxx or Cr6+), Polybrominated biphenyls (PBB), and Polybrominated diphenyl ether (PBDE).

Industry seeks efficient and economical measures to comply with RoHS. Dissolution in acid is commonly used to test and measure compositional qualities of sample material. This method has inherent disadvantages. Laser induced induce breakdown spectroscopy (LIBS) as well as other laser spectrometry methods provide a possible efficient and economical technique in determining or verifying elemental composition of products and other materials.

The LIBS type of spectrometry has been an unreliable and inexact measurement system since there is a large variation in the recorded data. A factor is the inconsistent plasma plume created by the pulse laser. Former LIBS type analysis was unsuccessful in matching known standards achieved with other analysis methods.

Accordingly, it is desirable to have a laser ablation spectrometry apparatus that can achieve valid quantitative and repeatable data.

SUMMARY OF THE INVENTION

In accordance with a first aspect of the present invention, a laser ablation spectroscopy apparatus is provided. A pulse laser is focused on a sample site to generate a plasma plume during a laser ablation process. The plasma plume is detected with a spectrometer and an intensified charge coupled device. A sample of material is coupled to a stage movable in the x, y and z directions using an array of x-y-z motors. A change in the height of the sample is detected using a sensor. Preferably, the sensor is a triangulation sensor. The apparatus includes a system computer for synchronizing the movement of the stage in the x, y and z direction during the laser ablation process. The height of the sample site can be automatically adjusted following each laser ablation. In one embodiment, the system computer includes a controller, application software and a graphical user interface (GUI).

In accordance with a second aspect of the present invention, a method of laser ablation spectroscopy is provided. The method includes a protocol of generating one or more laser ablations to a sample site. The spectral data of the total number of laser ablations for the sites are averaged together. In one embodiment, the total number of laser ablations for the sample site equals three laser ablations. The protocol includes laser ablating additional sample sites and averaging the spectral data of the total number of sample sites. In one embodiment, the total number of sample sites equals twenty sample sites.

Other features of the present invention will become apparent from consideration of the following description taken in conjunction with the accompanying drawings.

BRIEF DESCRIPTION OF THE DRAWINGS

The novel features of the invention are set forth in the appended claims. However, for purposes of explanation, several embodiments of the invention are set forth in the following figures.

DETAILED DESCRIPTION

In the following description, numerous details and alternatives are set forth for the purpose of explanation. However, one of ordinary skill in the art will realize that the invention can be practiced without the use of these specific details. In other instances, well-known structures and devices are shown in block diagram form in order not to obscure the description of the invention with unnecessary detail.

Figure 1:
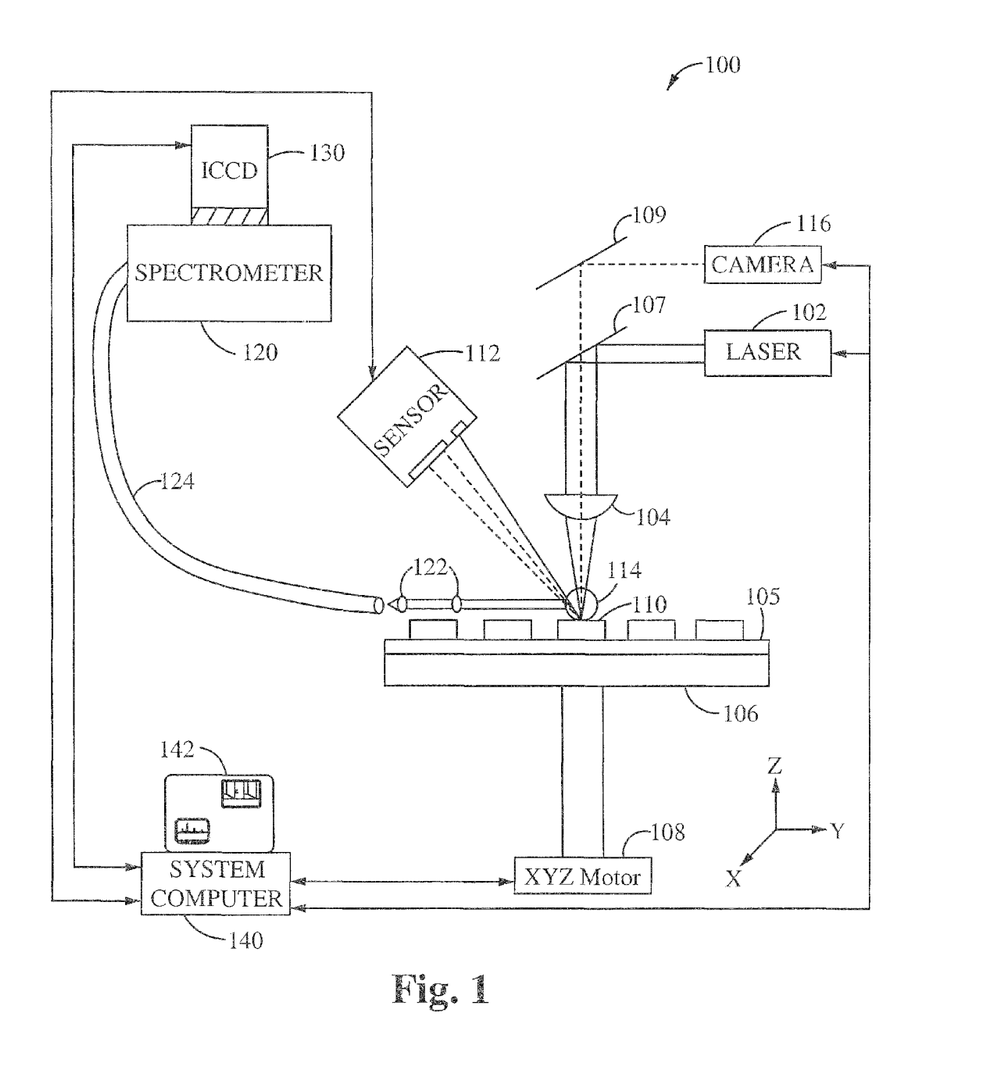
FIG. 1 illustrates a schematic diagram of a laser ablation apparatus according to an embodiment of the invention.

FIG. 1 shows a schematic overview of a laser ablation apparatus 100 according to the present invention. The apparatus 100 generally includes a pulse laser 102, a stage 106, a position sensor 112, a spectrometer 120 and a system computer 140. The apparatus 100 is configured to generate laser pulses from the pulse laser 102. The laser pulses are focused onto a sample 105 with a lens 104 to produce a plasma plume 114 of the sample 105 at a sample site 110. The position sensor 112 is electrically coupled with the system computer 140 for sending a displacement error signal to automatically correct positioning of the stage 106 during an ablating process as describe further below. The apparatus 100 can include a system frame for housing the various components described herein. The system frame can include an air filter for filtering contaminants produced during the ablating process.

The pulse laser 102 in an exemplary embodiment comprises a neodymium doped yttrium aluminum garnet (Nd:YAG) laser for generating energy in the near infrared region of the electromagnetic spectrum with a wavelength of 1064 nm. The pulse duration can be approximately 4 ns for generating a laser beam with a power density that can exceed one $GW/cm^2$ at a focal point or ablation impact point. The laser 102 can have a repetition rate of approximately 10 hz or alternately lower than 10 hz in some embodiments. Alternatively, the pulse duration can vary to tens or hundreds of nanoseconds. In another embodiment, the pulse duration can be shortened to ultra short femtoseconds. The lens 104 comprises an objective lens used to focus the laser beam on a surface of the sample site 110. The laser beam can be focused to a spot size of approximately 10-500 micrometers on the sample site 110. In an exemplary embodiment, the laser beam can be focused to a spot size of approximately 150-200 micrometers on the sample site 110.

In an alternative embodiment, a spark generator can be used as the ablation source instead of the pulse laser 102. An electric spark is passed through a sample material until the sample material reaches a temperature where characteristic spectral emissions can be detected. In an exemplary embodiment, the electric spark can be controlled in an argon atmosphere. A person of ordinary skill in the art can appreciate the construction of such spark generators in spark spectroscopy systems.

A dichroic mirror 107 is used for directing the laser beam toward the sample site 110 and a mirror 109 allows viewing of the sample site 110 using a video camera 116.

The stage 106 includes an attached array of 'x-y-z' motors 108 for providing translation of the stage 106 in a three dimensional space. The x-y-z motors can comprise suitable stepper motors as known by a person of skill in the art. In one embodiment, the stage 106 can have a translation rate of approximately 10 cm/s. The stage 106 can include a sample securing means.

Figure 1A:
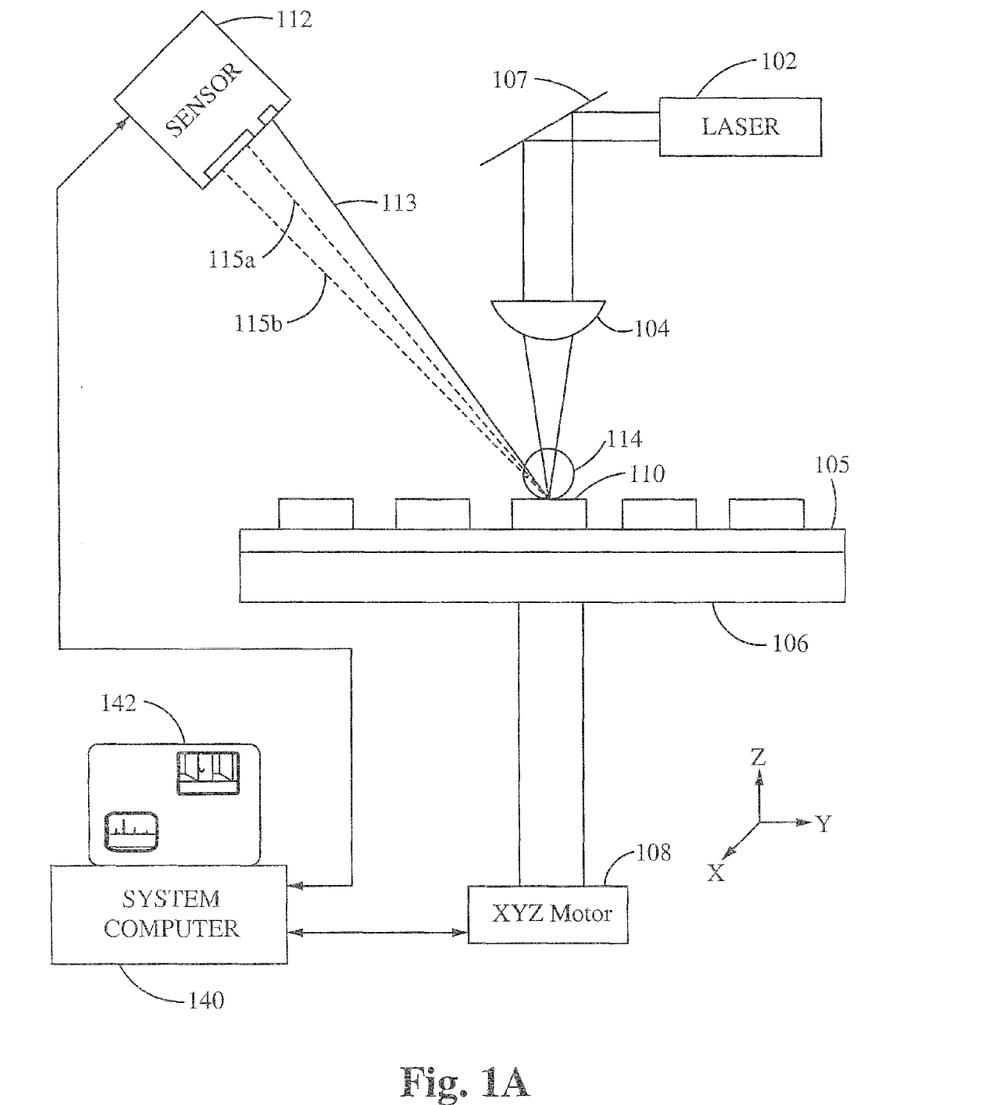
FIG. 1A illustrates a detail schematic diagram of a laser ablation apparatus according to an embodiment of the invention.

The position sensor 112 preferably comprises a laser triangulation sensor. The position sensor 112 preferably uses the principle of triangulation to determine changes in height of the stage 106 and the associated sample 105. As shown in greater detail in FIG. 1A, triangulation occurs when the position sensor 112 emits a triangulation laser beam 113 that is focused on the sample site and a first reflection 115*a* is sensed by a photodetector within the position sensor 112. A change in height of the sample site 110 causes a displacement in the triangulation laser beam 113 to produce a second reflection 115*b* and a displacement signal generated by the position sensor 112 is communicated to a system computer 140. The system computer 140 provides positioning information to maintain an optimum height of the sample site. The position sensor 112 can comprise a suitable laser displacement measuring device as known to a person of skill in the art. In one embodiment, the triangulation laser 113 coincides with a spot circle of the laser 102 generated at the sample site. The triangulation laser 113 can also be used as a targeting marker when selecting a specific point on the sample site 110 as seen with the video camera 116 as the triangulation laser 113 can produce a visible spot on the surface of the sample site 110.

The spectrometer 120 (FIG. 1) collects electromagnetic information from the plasma plume 114. The spectrometer 120 can be a monochromator or a polychomator. The electromagnetic information includes spectral information identifying an elemental composition of the sample site 110. A spectral range for the spectrometer 120 can be chosen to suit different applications. In an exemplary embodiment the spectral range can be approximately 35 nm for observing a portion of the electromagnetic wavelength range. Alternatively, the spectrometer 120 can detect electromagnetic radiation in a range of 200 to 900 nm. Collection optics 122 receive the light and plasma lumina generated from the plasma plume 114 and transmits the light and plasma lumina through a fiber cable 124 to the spectrometer 120. The collection optics 122 can be orientated horizontally as shown in FIG. 1. Alternatively, the collection optics 122 can be orientated at any angle above the sample 105 surface plane. A mirror (not shown) within the spectrometer 120 reflects the plasma lumina to a grating that disperses the plasma lumina.

An intensified charge coupled device (ICCD) or detector 130 is coupled with the spectrometer 120 for detecting the dispersed plasma lumina. The detector 130 provides the detected plasma lumina to the system computer 142. The system computer 140 generates spectral information from the plasma lumina of the laser plume 114. The spectral information includes intensity data representing elemental information and composition of the sample site 110. The spectral information can be produced on a display 142.

The detector 130 provides increased resolution and greater selectivity of the spectral information. The detector 130 includes a microchannel image intensifier plate. The intensifier plate is preferably gated during period of time when the plasma plume 114 emits characteristic atomic emission lines of the elements. This period coincides with an optimum plume luminance period. This period follows emission of continuum radiation. Continuum radiation lacks useful specific species or elemental information. In one embodiment, a delay generator (not shown) can be included to provided gating of the detector 130 to allow temporal resolution of the detector 130 response time. Alternative embodiments of the detector 130 can include a detector other than an ICCD, for example a suitable charge coupled device (CCD) or suitable photomultiplier. Accuracy of the spectrometer 120 and detector 130 in one embodiment can generate compositional data in the range of 20 ppm or less. Alternatively, the accuracy can be in the range of a few %. In another embodiment, the accuracy can be in the range of 1%, which is approximately 10,000 ppm.

The system computer 140 can include application software and a controller in the system computer 140 for providing synchronization of the laser 102, spectrometer 120, detector 130, position sensor 112 and the x-y-z motors 108 positioning of the stage 106. The system computer 140 is electrically coupled with the laser 102, spectrometer 120, detector 130, position sensor 112, the x-y-z motors 108 and the camera 116. The system computer 140 includes a display 142 for displaying spectral information. The system computer 140 can present the spectral data generated on the display 142. Alternatively, a separate personal computer can also be coupled with the system computer 140 for separately analyzing the spectral information. The system computer 140 can include a power controller to regulate power to all the apparatus 100 components.

The application software decodes the spectral information from the detector 130 and facilitates analysis of the spectral information and generates composition information of the sample 105. In one embodiment, the intensity data of an elemental peak is subtracted from background data of the elemental peak to calculate a change in intensity (delta I). The application software allows setting of certain parameters for performing the laser ablations of the sample site 110. A spot circle can be set as a parameter and can be consistently and precisely maintained through the laser ablation process described in further detail below. Alternatively, a z value for the sample site 110 can be set as a parameter and can be consistently and precisely maintained through the laser ablation process. The spot circle increases or decreases depending on the change in height of the sample site 110. Keeping the laser 102 spot circle precisely adjusted insures that the sample site 110 produces the plasma plume 114 with consistent optimum plume luminance. Height changes in the sample site can be detected by the position sensor 112 and a correction to the height of the sample site 110 is generated by the controller within the system computer 140. The application software and the controller generate correction signals to reposition the height of the stage 105 after each laser ablation of the sample site.

Figure 2:
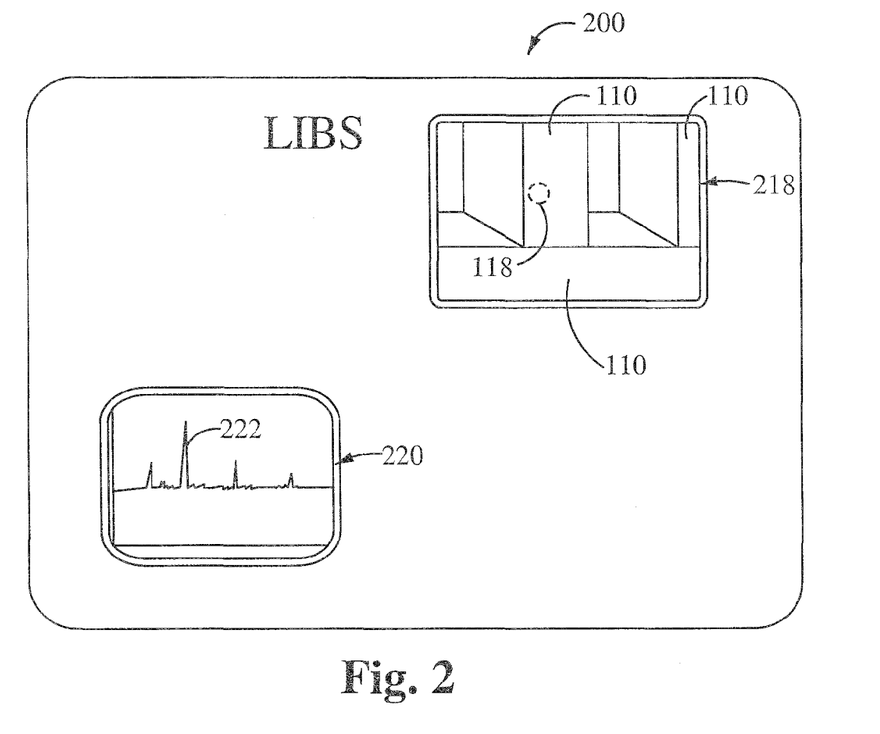
FIG. 2 illustrates a detail of a laser ablation graphical user interface according to an embodiment of the present invention.

FIG. 2 shows a representative graphical user interface (GUI) 200 according to an embodiment of the present invention. The GUI 200 includes a first data window 218 and a second data window 220. The first data window 218 provides real-time video of a sample site 110. A spot circle 118 can be observed on the sample site 110 during and following an ablation. The second data window 220 provides spectral information generated from the system computer 140. In an exemplary embodiment, the spectral information includes a waveform 222 representing intensity and wavelength data of a sample site ablation.

Figure 3:
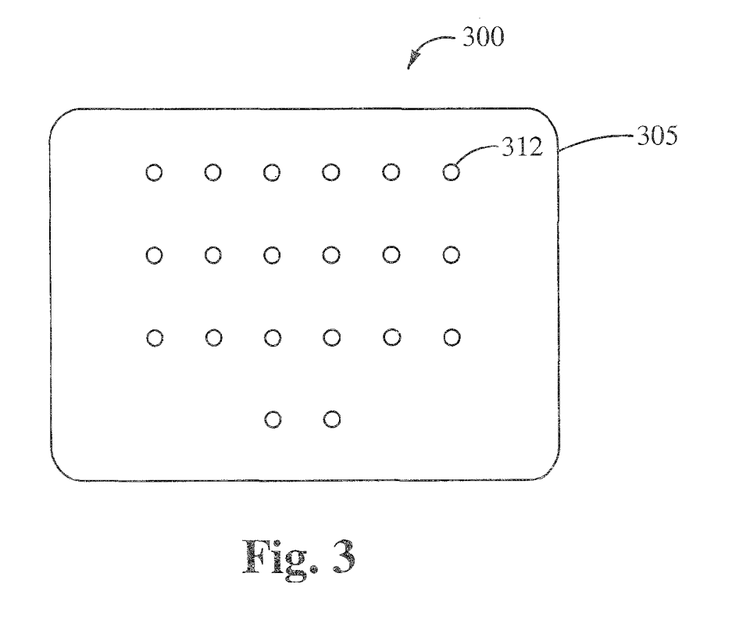
FIG. 3 illustrates a plan view of a testing protocol according to an embodiment of the invention.

FIG. 3 shows a top view 300 of a protocol for ablating a sample 305 according to an embodiment of the present invention. The protocol includes ablating multiple sample sites 312. In an exemplary embodiment, the sample sites can be uniformly and evenly distributed throughout a surface of the sample 305. Alternatively, the sample sites 312 can be randomly distributed through the surface of the sample site. The number of sample sites 312 ablated can vary depending on a particular sample or a particular application. In one embodiment, the number of sample sites comprises twenty. Alternatively, the number of sample sites can be ten or fewer. In another embodiment, the number of sample sites can be thirty or more.

The protocol 300 can include a specific number of pulse laser ablations per sample site 312. Heterogeneous material can include elements having varying thermal properties. A single shot laser ablation can vaporize disproportionately more volatile elements than the less volatile elements. Spectral information from a single ablation may not be a reliable indication of the composition of the sample 305. In an exemplary embodiment, the number of laser ablations per site comprises three laser ablations. Alternatively, the number of laser ablations per site comprises two. In another embodiment, the number of laser ablations per site comprises a single laser ablation. In still another embodiment, the number of laser ablations per site comprises four or more laser ablations.

Figure 4A:
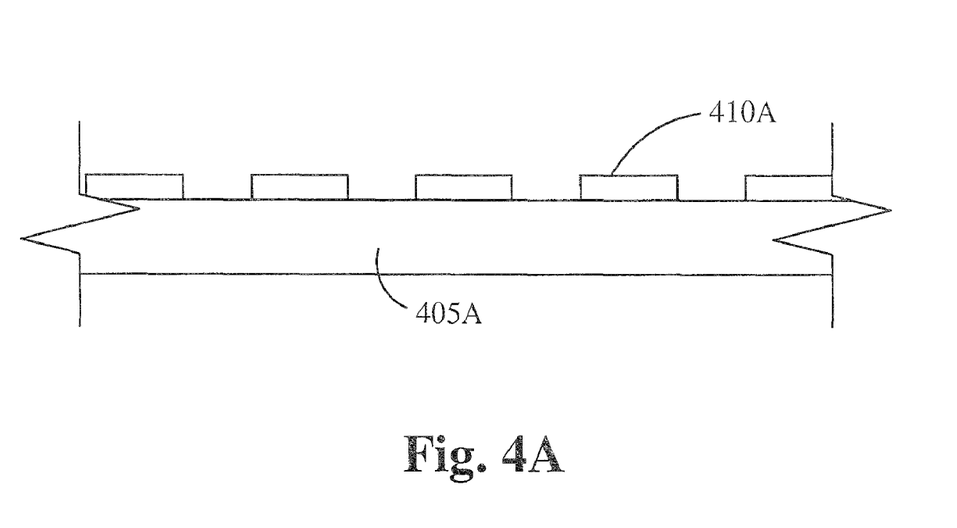
FIGS. 4A and 4B illustrate side views of a topology of a sample according to an embodiment of the invention.
Figure 4B:
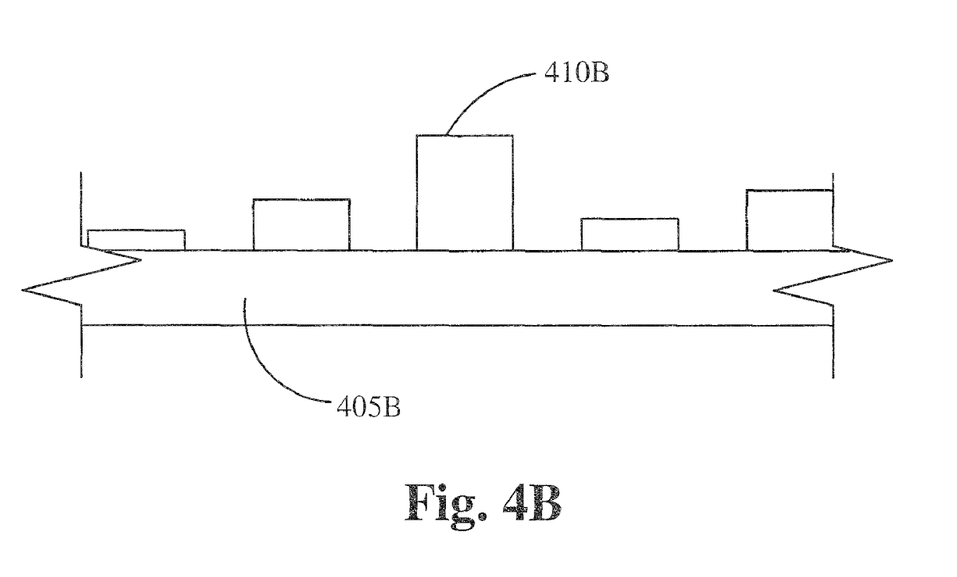

FIGS. 4A and 4B show side views of a first sample 405A and a second sample 405B according to an embodiment of the present invention. The first sample 405A comprises a material having sample sites 410A with substantially uniform topology. The height of the sample sites 410A are substantially the same. The second sample 405B, however, comprises a material having sample sites 410B with erratic or varying topology. The height of the sample sites 410B can be different. The apparatus 100 is configured to provide consistent spectral data for either the uniform sample sites 410A or sample sites 410B with varying heights. The system computer 140 adjusts the height of the stage 106 to achieve the optimal plasma lumina.

Figure 5:
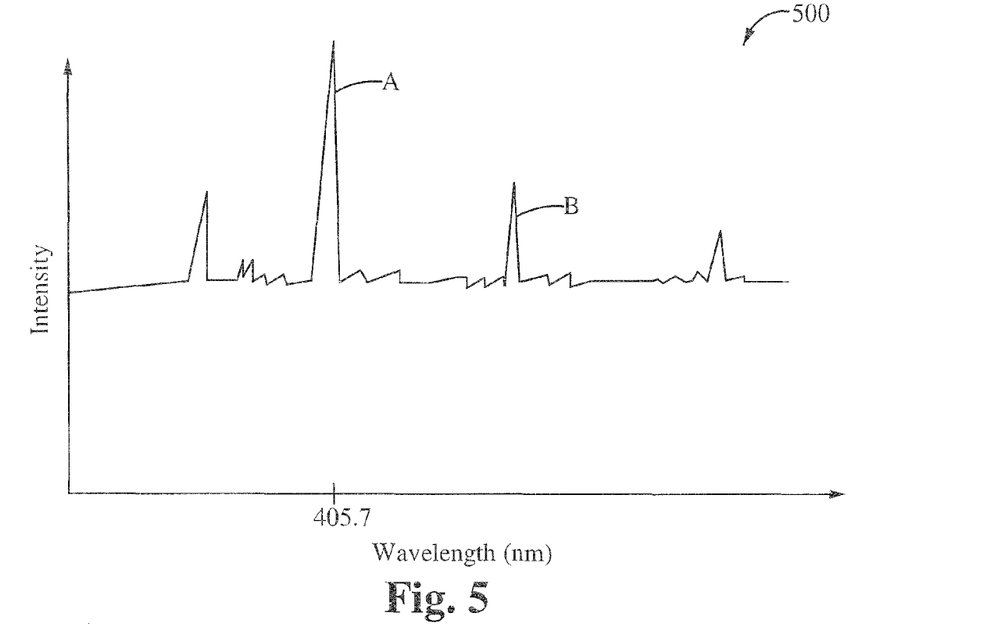
FIG. 5 illustrates a plot of spectral information according to an embodiment of the present invention.

FIG. 5 shows a plot 500 of spectral data according to an embodiment of the present invention. The plot 500 includes a waveform plotted along a wavelength (nm) versus an intensity (a.u.). An elemental peak 'A' can represent the spectral information for the element Lead (Pb). The elemental peak 'B' can represent spectral information of a different element.

Figure 6:
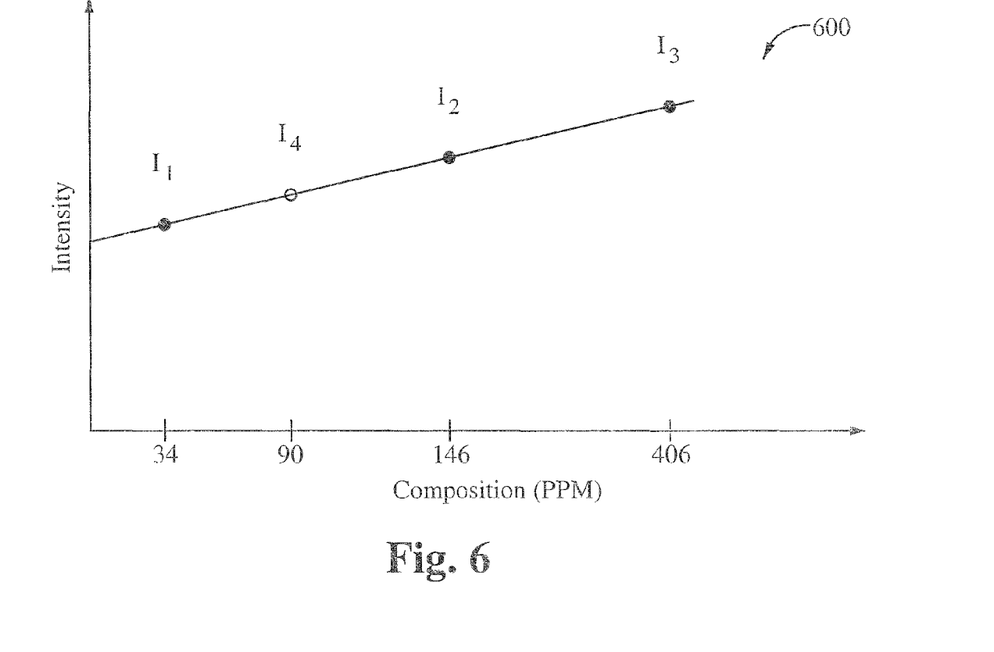
FIG. 6 illustrates a plot of intensities of known standards according to an embodiment of the present invention.

FIG. 6 shows a plot 600 of compositional data 600 according to an embodiment of the present invention. The plot 600 includes a waveform plotted along a composition (nm) versus an intensity (a.u.). The plot 600 is generated by performing laser ablation according to the method described herein on a known standard sample. The known standard produces intensities I1, I2 and I3 for associated elements at the respective compositions 34 ppm, 146 ppm and 406 ppm. Quantitative analysis of different elements of a particular sample is performed by comparing spectral data of the particular sample with the compositional data 600. For example, spectral information obtained from analysis with the apparatus 100 can include intensity 14. The quantity of the element can be approximated to 90 ppm.

Figure 7:
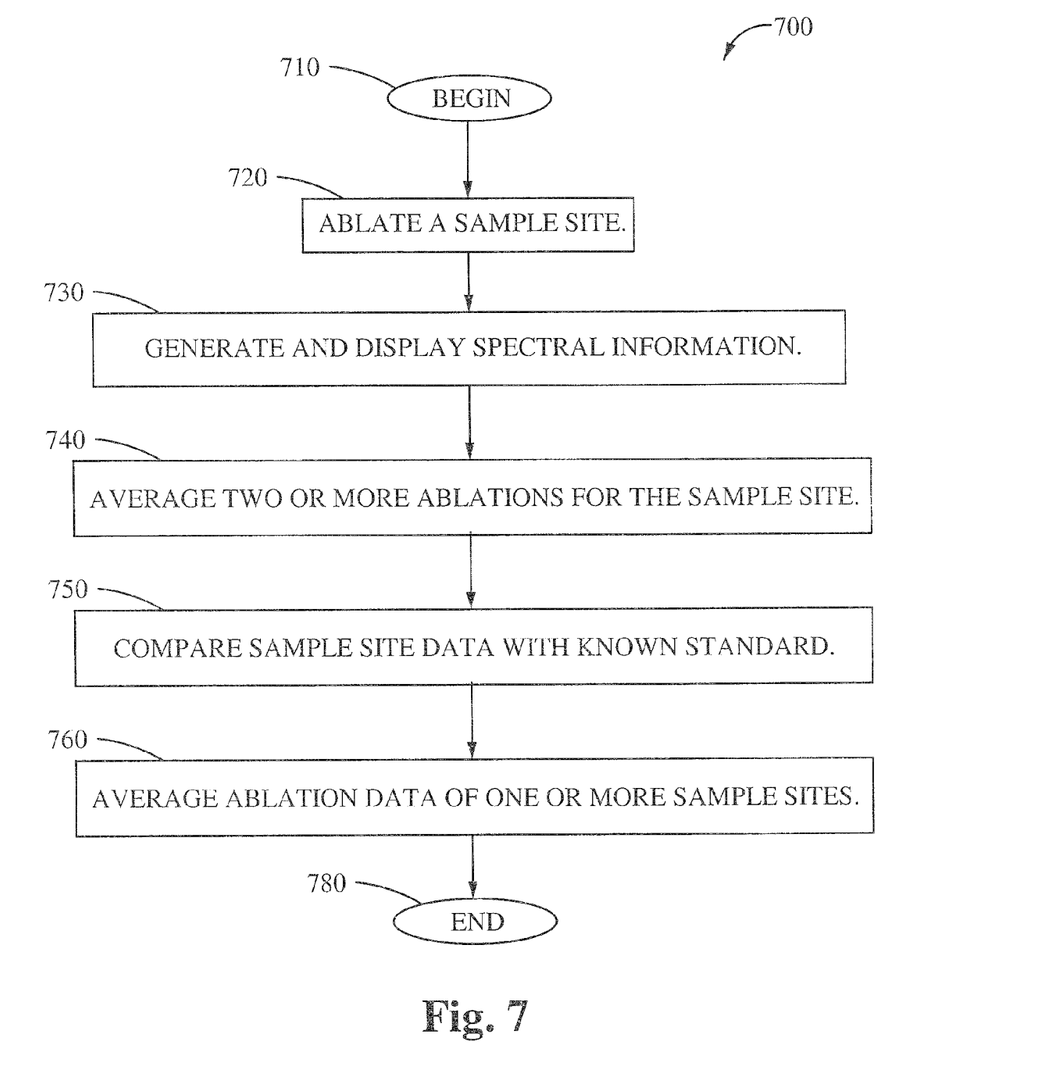
FIG. 7 illustrates a process flow diagram for a method of ablating according to an embodiment of the present invention.

FIG. 7 shows a process flow diagram for a method 700 of laser spectroscopy according to an embodiment of the present invention. The laser ablation apparatus 100 (FIG. 1) is used as an example. The method 700 begins at the step 710. In one embodiment, the method 700 can be fully automated using application software included in the system computer 140. A specific protocol can be entered into the application software instructing the application software of desired parameters or settings for the apparatus 100. Alternatively, the method 700 can be manually performed. At the step 720, a laser pulse is generated to ablate the sample site 110. A real-time video image of the sample site 110 is generated on a first window 218 of the GUI 200. The real-time video is received from the video camera 116. The plasma plume 114 is analyzed by the spectrometer 120 and the detector 130. The plasma lumina and the electromagnetic radiation generated by the plasma plume is optically communicated to the spectrometer 120 and detected by the detector 130. The position sensor 112 provides a displacement signal to the system computer 140 indicating any change in the height of the sample site 110. The system computer receives spectral information from the spectrometer 120 and the detector 130.

At the step 730, the system computer 140 generates spectral and wavelength information for presentation on the display 142. In one embodiment, intensity and wavelength data are represented as waveforms on the GUI 200. The waveform is presented in a second window 220 of the GUI 200 and includes the intensity and wavelength data. In another embodiment, a second waveform is superimposed on the first waveform 222 in the second window 220. The second waveform can include additional spectral information. For example, particle imaging information, tracking information or scaled or gated representations of the first waveform 222.

At the step 740, the steps 720 and 730 are repeated for each sample site on the sample. The spectral data for a total number of laser ablations for the sample site 110 can be averaged together. In an exemplary embodiment, the total number of laser ablations for the sample site 110 equals three laser ablations. The spectral data of the three laser ablations are averaged together to generate a 'site sum'. The site sum is a reliable and accurate representation of the elemental composition of the sample 105 at the sample site 110. Alternatively, the site sum comprises spectral data from two laser ablations. In another embodiment, the site sum comprises spectral data from one laser ablation. In still another embodiment, the site sum comprises spectral data from four or more laser ablations.

At the step 750, the site sum can be compared with spectral information generated from performing the method described herein on a known standard material. The known standard material comprises specific known elements at a known composition. Laser spectroscopy performed on the known elements generates known spectral data including known intensity values. An elemental composition for the sample site 110 can be approximated by comparing the site sum with the known standard spectral data.

At the step 760, the steps 720 through 750 can be repeated for one or more additional sample sites to generate additional site sums. The spectral data for the total number of site sums can then be averaged together. In an exemplary embodiment, the total number of site sums equals twenty. The spectral data of the twenty site sums can be averaged together to generate a 'sample sum'. The sample sum is a reliable and accurate representation of the elemental composition of the sample 105 as a whole. Alternatively, the total number of sites sums can be ten or fewer. In another embodiment, the number of sites sums can be thirty or more.

The apparatus 100 can perform laser ablation or laser induced breakdown spectroscopy (LIBS) on a variety of materials. The materials can be heterogeneous or homogeneous solids or semi-solids. Alternatively, the materials can comprise a liquid or even a gas. In another embodiment, the apparatus 100 can be used for LIBS on biological materials. Analysis of biological material can include building a library of known spectral signatures including elemental and compositional data for specific biological material. The spectrometer 120 can collect and detect with the detector 130 spectral information on a broad range from 200 to 900 nm. An unknown biological sample can be compared with the library to determine the biological substance. The method ends at the step 780.

In an alternative embodiment, the method 700 can be used in a remote configuration. The sample material is positioned in a location that is remote from the ablation source or laser. A telescopic device can be integrated with the apparatus 100 to provide optical coupling of plasma lumina. The generation and analysis of spectral data can proceed similarly as described herein. Other forms of laser ablation can be used within the scope of the present invention. Laser ablation inductively coupled plasma mass spectrometry (LA-ICP-MS) can be used as an alternative to the LIBS technique described herein.

While the invention has been described with reference to numerous specific details, one of ordinary skill in the art will recognize that the invention can be embodied in other specific forms without departing from the spirit of the invention. Thus, one of ordinary skill in the art will understand that the invention is not to be limited by the foregoing illustrative details, but rather is to be defined by the appended claims.

What is claimed is:

1. An apparatus for ablation spectroscopy, comprising:
   a stage to support a sample, the stage being operable to move in x and y directions of a plane and in a z (height) direction perpendicular to the plane;
   an ablation source operable to ablate material from a sample on the stage;
   a position sensor operable to generate a displacement signal proportional to a difference in height of a sample site;
   a stage position control circuit operable to automatically adjust a height of the stage based on the displacement signal;
   a detector coupled to a spectrometer, wherein the spectrometer and detector are operable to receive electromagnetic radiation emanating from the ablated material and to detect intensity and wavelength values of the electromagnetic radiation; and
   a computer operable to: receive the wavelength and the intensity values from the detector and spectrometer, determine a representation of a sample composition based on the received wavelength and the intensity values, and output and/or record the representation and/or wavelength and intensity values.

2. The apparatus of claim 1, wherein the ablation source is operable to produce a luminous plasma plume emanating electromagnetic radiation characteristic of chemical species in the sample.

3. The apparatus of claim 2, wherein the ablation source comprises a pulsable laser operable to ablate the material and produce the luminous plasma plume.

4. The apparatus of claim 1, further comprising a triangulation laser, wherein the stage position control system comprises an array of motors operable to move the stage a predetermined amount.

5. The apparatus of claim 1, wherein the position sensor displacement signal depends on a laser triangulation of the sample site.

6. The apparatus of claim 5, wherein the triangulation laser is operable to provide a visible targeting marker on the sample site.

7. The apparatus of claim 1, wherein the detector is operable to be insensitive to electromagnetic radiation during one time interval, and be switched on to receive the electromagnetic radiation during another different time interval.

8. The apparatus of claim 1, wherein the detector comprises an electronically gateable device.

9. The apparatus of claim 1, wherein the apparatus is operable to determine an element concentration of 20 parts per million or less in the sample.

10. The apparatus of claim 1, wherein the apparatus includes a controller operable to synchronize the positioning of the stage, the ablation of the sample, and the receiving electromagnetic radiation by the spectrometer and detector.

11. The apparatus of claim 1, further comprising an inductively coupled plasma mass spectrometer.

12. A method of consistent sample analysis using laser ablation, the method comprising:
    placing an analysis sample on a stage in a laser ablation apparatus, wherein the stage is operable to move at least in a height direction (z-direction) perpendicular to a plane of the stage; and
    performing a plurality of laser ablations of a site on the analysis sample, wherein each laser ablation produces a luminous plasma plume comprising ablated material;
    collecting spectral data from each of the analysis sample site laser ablations; and
    generating a representation of the analysis sample composition based on an average of the spectral data collected from the laser ablations of the analysis sample site;
    wherein performing the plurality of laser ablations comprises:
    moving the stage into a position operable to effectuate a first laser ablation of the analysis sample site;
    sensing a change in the height of the analysis sample site before performing a next laser ablation of the analysis sample site; and
    repositioning the height of the stage responsive to sensing the change in the height of the analysis sample site, before performing the next laser ablation.

13. The method of claim 12, further comprising:
    placing a known standard sample on the stage;
    performing one or more laser ablations of the known standard sample, wherein each laser ablation of the known standard sample produces a luminous plasma plume comprising ablated standard sample material;
    collecting spectral data from the one or more known standard sample ablations; and
    generating a representation of the known standard sample composition based on the spectral data collected from the one or more known standard sample ablations;
    wherein the representation of the analysis sample composition depends on a comparison of the analysis sample spectral data with the representation of the known standard sample composition.

14. The method of claim 13, wherein the spectral data from the known standard sample and the spectral data from the analysis sample comprise respective spectral intensity and wavelength values, and the representation of the analysis sample composition depends on a predetermined chemical composition of the known standard sample.

15. The method of claim 14, wherein the predetermined chemical composition of the known standard sample is an elemental composition; and the representation of the analysis sample composition is based on identifying elemental intensity peaks in the analysis sample spectral data, applying a correction to an identified elemental peak intensity using background data, and comparing the identified elemental peak intensity with a corresponding elemental peak intensity in the representation of the known standard sample composition.

16. The method of claim 12, further comprising:
performing at least a first laser ablation at a second different analysis sample site;
sensing a difference in height between the first analysis sample site and the second analysis sample site; and
moving the stage into a position operable to effectuate the first laser ablation at the second sample site;
wherein moving the stage into the position at the second sample site includes repositioning the height of the stage based on the difference in height between the first sample site and the second sample site.

17. The method of claim 16, wherein:
one or more laser ablations are performed at each different site among a plurality of different analysis sample sites;
spectral data are collected from the one or more laser ablations at each of the different analysis sample sites, and the collected spectral data from each of the different analysis sample sites is averaged together to generate a site sum representation of elemental composition at each respectively distinct analysis sample site, and
each of the site sum representations of the elemental composition at a distinct analysis sample site are averaged together to generate a sample sum representation of the elemental composition of the analysis sample as a whole.

18. The method of claim 12, wherein the laser ablation comprises laser induced breakdown.

19. The method of claim 12, wherein sensing the change in the height of the analysis sample site is performed using a position sensor operable to generate a displacement signal proportional to the change.

20. The method of claim 12, wherein the sensing comprises laser triangulation of the analysis sample site.

21. The method of claim 19, wherein the laser ablation apparatus further comprises an array of motors operable to move the stage in x and y directions of a plane and in a z (height) direction perpendicular to the plane, and a substrate control circuit operable to receive the displacement signal from the position sensor and move the stage with the array of motors, wherein the repositioning is performed with the substrate control circuit.

22. The method of claim 21, wherein the laser ablation apparatus further comprises a triangulation laser operable to produce a visible spot on the analysis sample site, and the sensing the change in height depends on a triangulation using the triangulation laser.

23. The method of claim 22, wherein the laser ablation apparatus is coupled to a display device, and the method further comprises displaying a real time video image showing the visible triangulation laser spot at the analysis sample site in a first graphical user interface window on the display device, and displaying information based on the collected spectral data in a second graphical user interface window on the display device.

24. The apparatus of claim 2, wherein the detector is operable to be insensitive to the electromagnetic radiation from the plasma plume in a time period when a ratio of continuum radiation relative to characteristic atomic line emission is relatively large, and be switched on to receive the electromagnetic radiation from the plasma plume during a different time period when the ratio of continuum radiation relative to characteristic atomic line emission is relatively small.

25. The apparatus of claim 8 wherein the electronically gateable device comprises a charge coupled device.

26. The apparatus of claim 8 wherein the electronically gateable device comprises a photomultiplier.

27. The apparatus of claim 9 wherein the determined element concentration is within a few percent accuracy.

28. The apparatus of claim 3, wherein the apparatus is operable to perform a plurality of ablations at one selected site of the sample, and the stage position control system is operable automatically adjust the height of the stage to maintain one preselected laser spot size in performing each of the ablations.

29. The apparatus of claim 2, wherein the ablation source comprises a laser operable to ablate the material and produce a luminous plasma plume, the apparatus is operable to perform at least one ablation at each sample site among a plurality of different sample sites, and the stage position control system is operable to maintain a preselected laser spot size in performing each of the sample site ablations.

30. The apparatus of claim 3, wherein the apparatus is operable to set a z-value for the sample site as a parameter for ablation at the sample site, and the stage position control system is operable to effectuate the z-value in performing each ablation at the sample site.

31. The apparatus of claim 5 wherein the position sensor comprises a laser displacement measuring device including a triangulation laser and a photodetector; wherein:
the laser displacement measuring device is operable to focus a triangulation laser beam on the sample site and sense a first reflection of the laser beam using the photodetector;
a change in the height of the sample site is operable to produce a second reflection of the triangulation laser beam; and
the displacement signal is depends on a displacement between the first reflection and the second reflection.

32. The apparatus of claim 31 wherein the triangulation laser is operable to produce a visible spot on a surface of a sample site.

33. A method of ablation spectroscopy material analysis, comprising:
placing a sample on a stage operable to move in the x and y directions of a plane, and in a height direction (z-direction) perpendicular to the plane,
performing a plurality of ablations of a surface of the sample at first and second selected sample sites, wherein each ablation is operable to produce a luminous plasma plume; and
collecting spectral data from each of the luminous plasma plumes;
wherein performing the plurality of ablations comprises:
performing a first ablation of material at a first selected sample site before repositioning a height of the stage and performing a second ablation of material at a second selected sample site, after the repositioning.

34. The method of claim 33 wherein obtaining mutually consistent spectral data from the first ablation at the first selected sample site and the second ablation at the second selected sample sites depends on the repositioning.

35. The method of claim 33 wherein the first selected sample site and the second selected sample site are substantially the same site.

36. The method of claim 33 wherein the first selected sample site and the second selected sample site are different sites.

37. The method of claim 33 further comprising providing a displacement signal proportional to a difference between a height of the first selected sample site before the first ablation, and a height of the second selected sample site before the second ablation, wherein the height of the stage is automatically repositioned before the second ablation and the repositioning depends on the displacement signal.

38. The method of claim 33 further comprising determining a representation of sample composition based on the collected spectral data, using instructions performed by a computer, and displaying the representation of sample composition and/or at least a portion of the collected spectral data on an electronic display device.

39. A method of providing a representation of an analysis sample composition based on spectral data from the analysis sample and spectral data from a known standard sample, the method comprising:
   placing the analysis sample on a stage operable to move in the x and y directions of a plane, and in a z-height direction perpendicular to the plane,
   selecting at least first and second sites of the analysis sample;
   at each selected site of the analysis sample, performing at least one ablation operable to produce an associated luminous plasma plume comprising material ablated from the respective analysis sample site;
   collecting spectral data from the luminous plasma plume in each respective ablation of the analysis sample;
   placing the known standard sample on the stage;
   selecting one or more sites on the standard sample;
   at each selected site of the standard sample, performing one or more ablations operable to produce an associated luminous plasma plume comprising material from the standard sample;
   collecting spectral data from the one or more ablations at the selected sites on the standard sample; and
   determining a representation of at least one selected analysis sample site composition, wherein the representation of each respective analysis sample site composition depends on the spectral data collected from the one or more ablations of the respective analysis sample site and on the spectral data collected from the one or more ablations of the one or more selected sites on the standard sample.

40. The method of claim 39 wherein the first selected sample site and the second selected sample site are substantially the same site.

41. The method of claim 39 wherein the first selected sample site and the second selected sample site are different sites.

42. The method of claim 39, further comprising repositioning a height of the stage after performing a first ablation of the analysis sample and before performing a second ablation of the analysis sample.

43. The method of claim 42 wherein the first ablation is performed at the first selected analysis sample site, the second ablation is performed at the second selected analysis sample site, and collecting mutually consistent spectral data from the first and second ablations depends on the repositioning.

44. The method of claim 42 further comprising providing a displacement signal depending on a difference between a height of a first selected analysis sample site prior to the first ablation and a height of the second selected analysis sample site prior to the second ablation, wherein the repositioning is based on the displacement signal.

45. The method of claim 44 wherein the displacement signal is proportional to the difference.

46. The method of claim 44 wherein the repositioning is performed using a control circuit.

47. The method of claim 39, further comprising repositioning a height of the stage after performing a first ablation of the standard sample and before performing a second ablation of the standard sample, whereby mutually consistent spectral data are collected from the first and second ablations of the standard sample.

48. The method of claim 39, wherein the spectral data from each of the associated luminous plasma plumes is exclusively collected during a respective time period when an intensity of characteristic atomic line emission is relatively high and an intensity of continuum radiation is relatively low.

* * * * *